United States Patent
Clough et al.

[11] Patent Number: 5,846,833
[45] Date of Patent: Dec. 8, 1998

[54] METHOD AND APPARATUS FOR TESTING A NON-HYDROCARBON REFRIGERANT

[75] Inventors: Warren R. Clough, Cicero; Lowell E. Paige, Pennellville, both of N.Y.; John Attanasio, Indianapolis, Ind.; William A. Faris, Syracuse, N.Y.; H. Harvey Michels, W. Hartford; David A. Condit, Avon, both of Conn.

[73] Assignee: Carrier Corporation, Syracuse, N.Y.

[21] Appl. No.: 785,722

[22] Filed: Jan. 17, 1997

[51] Int. Cl.$^6$ .................................................. G01N 33/00
[52] U.S. Cl. ........................... 436/139; 436/167; 422/58; 422/86; 422/88; 62/125; 62/127; 62/129
[58] Field of Search .................................. 436/139, 167; 422/58, 86, 88, 104; 62/125, 127, 129

[56] References Cited

U.S. PATENT DOCUMENTS

| | | | |
|---|---|---|---|
| 4,417,451 | 11/1983 | Spauschus | 62/129 |
| 4,803,843 | 2/1989 | Otto | 62/129 X |
| 4,923,806 | 5/1990 | Klodowski | 436/39 |
| 5,071,768 | 12/1991 | Klodowski | 436/39 |
| 5,092,911 | 3/1992 | Williams et al. | 95/117 |
| 5,174,964 | 12/1992 | Klodowski et al. | 422/88 |
| 5,345,774 | 9/1994 | Mount | 62/127 |
| 5,363,661 | 11/1994 | Condit et al. | 62/129 X |
| 5,377,496 | 1/1995 | Otto et al. | 62/129 |
| 5,419,177 | 5/1995 | Pastorello | 73/23.4 |

*Primary Examiner*—Maureen M. Wallenhorst
*Attorney, Agent, or Firm*—William W. Habelt

[57] ABSTRACT

A method for testing a non-hydrocarbon refrigerant, such as CFC-12 or HFC-134a, in a closed system for hydrocarbons, HCFC-22 refrigerant and ammonia is provided wherein a sample of the non-hydrocarbon refrigerant is withdrawn from the closed system, the pressure of the sample is measured and a metered portion of the sample is passed through a test apparatus (20) including a testing tube (30), a testing tube holder (40) for supporting the testing tube (30) and outfitted with a vent (48) to the atmosphere, and a pressure gauge (70) for indicating the pressure of the sample withdrawn. A medium (38) for indicating the presence of hydrocarbons in the sample flow passing through the testing tube is deposited on a surface disposed in the testing tube. The presence of undesired HCFC-22 refrigerant in the CFC-12 or HFC-134a is indicated by a higher pressure reading on the pressure gauge (70). Finally, the presence of ammonia is sensed by its characteristic pungent odor as the refrigerant sample flow is vented to the atmosphere.

4 Claims, 2 Drawing Sheets

METHOD AND APPARATUS FOR TESTING A NON-HYDROCARBON REFRIGERANT

BACKGROUND OF THE INVENTION

The present invention relates generally to testing refrigerants for the presence of contaminants and, more particularly, to testing non-hydrocarbon refrigerants, specifically CFC-12, a chlorofluorocarbon, and HFC-134a, a hydrofluorocarbon, for the presence of three specific contaminants: namely, hydrocarbons, HCFC-22, and ammonia.

Certain non-hydrocarbon compounds, such as CFC-12, HFC-134a, and blends of HFC and/or HCFC, that is hydrochlorofluorocarbon compounds, are commonly used as refrigerants in various types of air conditioning and refrigeration systems, including automotive air conditioning systems and other mobile air conditioning refrigeration systems. These refrigerants have different properties such as boiling point and vapor pressure that dictate to a great extent a given refrigerant's suitability for a particular application. Refrigeration systems are generally classified as either high pressure systems or low pressure systems depending on the system operating pressure. As each refrigerant has a particular vapor pressure characteristic, the refrigerants used in these systems are therefore commonly referred to as either high pressure or low pressure refrigerants depending upon the operating pressure of the system in which they are used. The vapor pressure of a refrigerant at normal ambient temperatures can range from about 140 kPa (about 20 psi) for a low pressure refrigerant to over 1400 kPa (about 200 psi) for a high pressure refrigerant, depending upon the refrigerant.

In air conditioning or refrigeration systems, a small amount of compressor lubricating oil circulates with the refrigerant. Both refrigerants and lubricating oils tend to absorb water to some fine extent. Water introduced into an air conditioning or refrigeration system will therefore be absorbed to some extent into and circulate with the refrigerant and oil. Excessive water within the system can cause ice to form, promote corrosion of metal components of the system, damage motor insulation in hermetic compressors or damage other system components. Water can be present in a refrigeration or air conditioning system due to improper drying of equipment during manufacture or servicing, leaks in the system, wet refrigerant, water contaminated oil, oxidation of hydrocarbons in the oil and decomposition of cellulose insulation in hermetically sealed units. To assure efficient system operation and prevent damage, it is necessary to detect the presence of water contamination and remove it from the system.

Acid contamination can also be present in a refrigeration or air conditioning system due to chemical breakdown of the refrigerant caused by overheating in the compressor. The typical acid contaminants due to refrigerant breakdown are hydrochloric and/or hydrofluoric acid. Other acids can be produced as the decomposition products of oil, insulation, varnish, gaskets and adhesives. Like water, some of these acids can be carried through the system with the refrigerant and build up to levels which can be indicative of the failure or potential failure of system components.

Oxygen, nitrogen and carbon dioxide can also be present in a refrigeration or air conditioning system as a result of incomplete system evacuation before refrigerant fill or low side in-leakage. In addition, carbon dioxide can be present due to the overheating and resultant decomposition of organic insulation materials such as may occur in a motor burnout. Carbon monoxide can also be formed as a result of overheated insulation. Hydrogen may be present as a result of bearing wear. Excessive concentrations of these noncondensable gases in the system can reduce system efficiency.

In U.S. Pat. No. 5,071,768 to Klodowski, there is disclosed a method and apparatus for testing a refrigerant contained in a closed system in a single testing operation for the presence and concentration of water, inorganic acids, volatile organic acids, oxygen, carbon dioxide, carbon monoxide and hydrogen or any one or combination of contaminants taken from that group. As disclosed therein, in a test for a contaminant, a continuous small sample flow of refrigerant is withdrawn from the system and directed through a testing tube containing a demister section to separate any oil that is entrained in the refrigerant, a water removal section and one or more contaminant indicating sections. The water removal section may also indicate the presence and concentration of water contamination. The disclosed apparatus includes means for reducing, if necessary, system pressure to a pressure near ambient before the sample flow enters the testing tube. The apparatus also includes a means for directing all of the sample flow through the tube and may include a testing tube holder that provides support and protection for the tube and, as well, means for providing indication of sample flow. The testing tube and other components of the apparatus are prepared for a test by placing them in flow communication with the system to be tested, with the pressure reducing means between the system and the tube. Means for isolating the removal and indicating media from the environment external to the testing tube are removed from the tube before the test is commenced and/or by breaching at the commencement of the test. The presence of a given contaminant is indicated by a color change in an appropriate indicating medium in the testing tube and the concentration is determined by comparison of the changed color of the medium to a color chart and/or the extent of propagation of the color change through the medium.

Non-hydrocarbon refrigerants, such as CFC-12 and HFC-134a, may be contaminated with hydrocarbon compounds, HCFC-22, which is a common hydrochlorofluorocarbon refrigerant, and/or ammonia. These compounds have become the primary contaminants found in CFC-12 and HFC-134a refrigerant based mobile or automotive air conditioning systems. As these contaminants can adversely impact system performance, it would be desirable to have a method and apparatus for detecting their presence in a non-hydrocarbon refrigerant in a closed system without removing all of the refrigerant from the system.

Another contamination issue involves several refrigerant blends, containing combinations of HFCs, HCFCs and hydrocarbons, that have been proposed as substitutes for CFC-12 and HFC-134a. These blends, like the specific contaminants mentioned above, are considered contaminants with regard to reclaim equipment. Commercial reclaim equipment presently is geared to only handle CFC-12 or HFC-134a. Service centers are as concerned about contaminating reclaimed CFC-12 and HFC-134a with any of these alternatives as they are contaminating reclaimed CFC-12 and HFC-134a with hydrocarbons, HCFC-22 and ammonia. Thus, it is desirable to have a method and apparatus which can not only detect the presence of specific contaminants, but additionally, the aforementioned alternatives. This extends the utility of the method and apparatus beyond diagnosing air conditioning performance problems to providing an indication used to prevent contaminating valuable CFC-12 and HFC-134a reclaim stock and any respective recovery equipment.

SUMMARY OF THE INVENTION

It is an object of one aspect of the present invention to provide a method for testing a low pressure nonhydrocarbon refrigerant in a closed system, such as an air conditioning or refrigeration system, to detect hydrocarbon compounds, HCFC-22 and/or ammonia, without removing all of the refrigerant charge from the system.

It is an object of another aspect of the present invention to provide a method for testing a non-hydrocarbon refrigerant in a closed system, such as an air conditioning or refrigeration system, to detect hydrocarbon refrigerant blends without removing all of the refrigeration charge from the system.

A method for testing a non-hydrocarbon refrigeration in a closed system for hydrocarbons, HCFC-22 and ammonia is provided wherein a sample flow of the non-hydrocarbon refrigerant is withdrawn from the closed system, the pressure of the sample is measured and a metered portion of the sample flow is passed through a testing tube wherein there is provided a medium for indicating the presence of hydrocarbons in the sample flow passing through the testing tube. Preferably, the medium for indicating the presence of hydrocarbons comprises a chemical deposited on a surface disposed in the testing tube, the chemical having the characteristic of undergoing a change in color when contacted by a hydrocarbon. Finally, the presence of ammonia is sensed by its characteristic pungent odor as the refrigerant sample flow is vented to the atmosphere.

It is an object of a further aspect of the present invention to provide an apparatus for testing a low pressure non-hydrocarbon refrigerant in a closed system, such as an air conditioning or refrigeration system, to detect hydrocarbon compounds, HCFC-22 and/or ammonia without removing all of the refrigerant charge from the system.

It is an object of a still further aspect of the present invention to provide an apparatus for testing a non-hydrocarbon refrigerant in a closed system, such as an air conditioning or refrigeration system, to detect hydrocarbon-containing refrigerant blends without removing all of the refrigeration charge from the system.

An apparatus is provided for testing a non-hydrocarbon refrigeration in a closed system for hydrocarbon contaminants in a sample flow of the non-hydrocarbon refrigerant withdrawn from the closed system. The test apparatus comprises a testing tube, a testing tube holder for supporting the testing tube and outfitted with a vent to the atmosphere, and a pressure gauge for indicating the pressure of the sample withdrawn. A medium for indicating the presence of hydrocarbons is disposed in the testing tube in the flow path of the sample flow passing through the testing tube. Preferably, the medium for indicating the presence of hydrocarbons comprises a chemical deposited on a surface disposed in the flow path defined within the testing tube, the chemical having the characteristic of undergoing a change in color when contacted by a hydrocarbon.

BRIEF DESCRIPTION OF THE DRAWINGS

The foregoing objects and various aspects, features and advantages will become more apparent and be further understood from the following description of a preferred embodiment of present invention, with reference to the accompanying drawings, which form a part of the specification, wherein.

Throughout the drawings, like reference numbers designate like or corresponding elements and the arrow A denotes the direction of refrigerant sample flow during a test.

DESCRIPTION OF THE PREFERRED EMBODIMENTS

Figure 1:
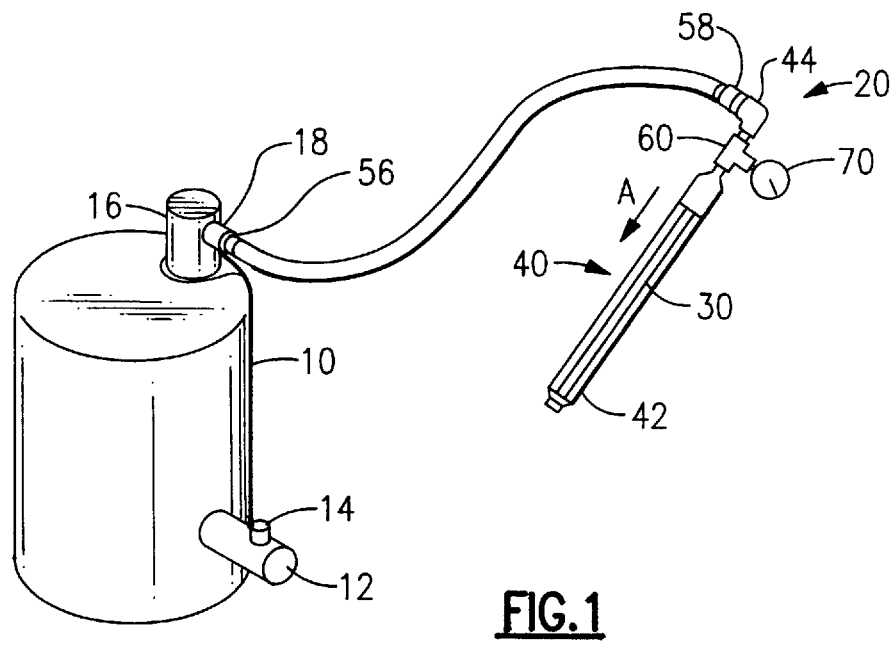
FIG. 1 is a perspective view of a preferred embodiment of the test apparatus of the present invention illustrated in use in connection with testing refrigerant of an air conditioning system.
Figure 2:
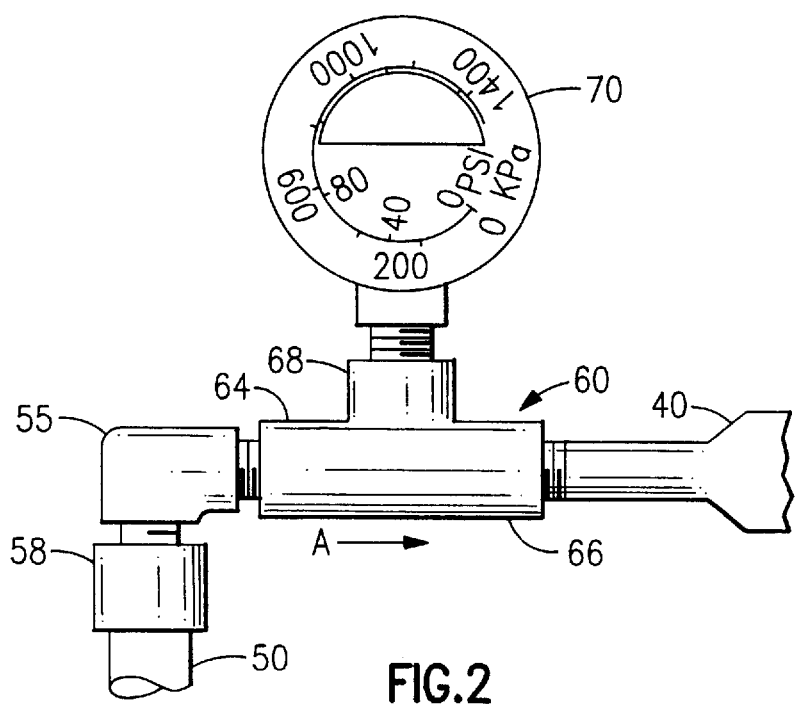
FIG. 2 is an exploded view of the upstream portion of the test apparatus of FIG. 1.

The test apparatus 20 of the present invention is depicted in FIG. 1 being used in connection with an automotive air conditioning system having a compressor 10. It is to be understood, however, that the test apparatus of the present invention may be utilized for detecting hydrocarbon contaminants in various closed systems, including but not limited to residential or commercial air conditioning systems and stationary or mobile refrigeration systems, containing a non-hydrocarbon refrigerant, such as for example CFC-12 or HFC-134a refrigerants. Compressor 10 has suction line 12 containing service valve 14 and a discharge line 16 containing service valve 18. The figure illustrates the invention in use to test for the presence of contaminants in the refrigerant leaving compressor 10 via discharge line 16. The test apparatus 20 of the present invention may be used to sample the refrigerant at other points in the system, such as for example at the suction line 12, and may be used to test refrigerants in both high and low pressure systems.

Referring now to FIGS. 1 through 6, the test apparatus 20 comprises a testing tube 30, a testing tube holder 40 that provides a support housing for the testing tube 30 and a pressure gauge 70. A transitional tee 60 is provided for connecting the pressure gauge 70 in line upstream of the testing tube holder 40. The transitional tee 60 is of the conventional type having a main flow passageway therethrough with a secondary flow branching off the main flow passageway and three threaded connection fittings 64, 66 and 68, each of which is depicted in the drawing as an internally threaded fitting, but may alternatively comprise an externally threaded fitting. The first fitting 64 is mated to one end of a threaded elbow 55 and the second connector 58 on the end of a refrigerant sample flow hose 50 is mated to the other end of the threaded elbow 55. The second fitting 66 is mated to the inlet end of the testing tube holder 40. The pressure gauge 70 is connected via the third fitting 68 in flow communication with the secondary flow passageway of the transitional tee 60 as to provide for the measurement and indication of the pressure of the refrigerant sample flow passing through the main flow passageway of the transitional tee 60 when a test sample is taken.

The refrigerant sample flow hose 50, which may comprise any conventional high pressure, flexible refrigerant suitable for the pressure and chemical composition of the refrigerant in use, when connected as hereinafter described, provides a flow path for the refrigerant sample flow to pass from the closed system to the test apparatus 20. The refrigerant sample flow hose 50 includes a first connector 56 at one end thereof for connecting to the compressor service valve or outlet valve on the closed system, and a second connector 58 at the other end thereof for connecting directly to the test apparatus 20 or to the elbow 55 directly upstream of the test apparatus 20. When the test apparatus 20 is to be utilized in connection with automotive air conditioning systems, the first connector 56 advantageously comprises a quick disconnect fitting of a conventional type suitable for mating with the service fittings customarily employed on automotive air conditioning systems. If the test apparatus 20 is to be utilized in connection with conventional residential or commercial building air conditioning or refrigeration systems, the first connector 56 advantageously may comprise a Schraeder type fitting.

Figure 3:
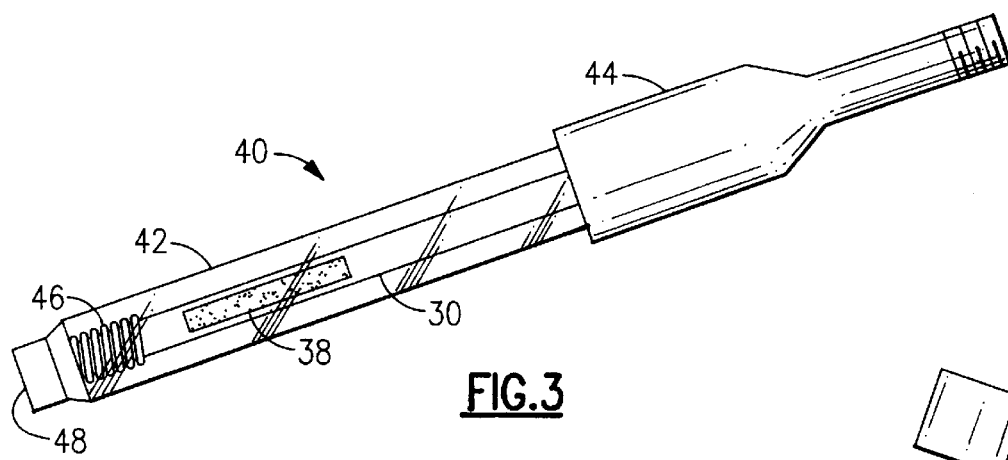
FIG. 3 is an exploded view of a contaminant testing tube holder apparatus and a contaminant testing tube of the embodiment depicted in FIG. 1.
Figure 4:
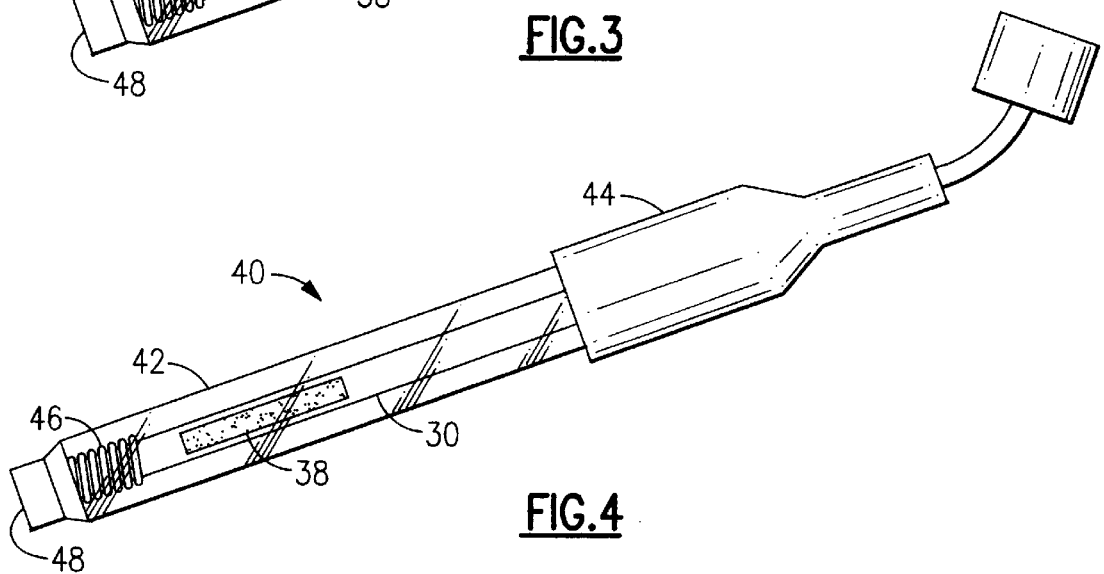
FIG. 4 is an exploded view of a second embodiment of the contaminant testing tube holder apparatus of the test apparatus of the present invention.
Figure 5:
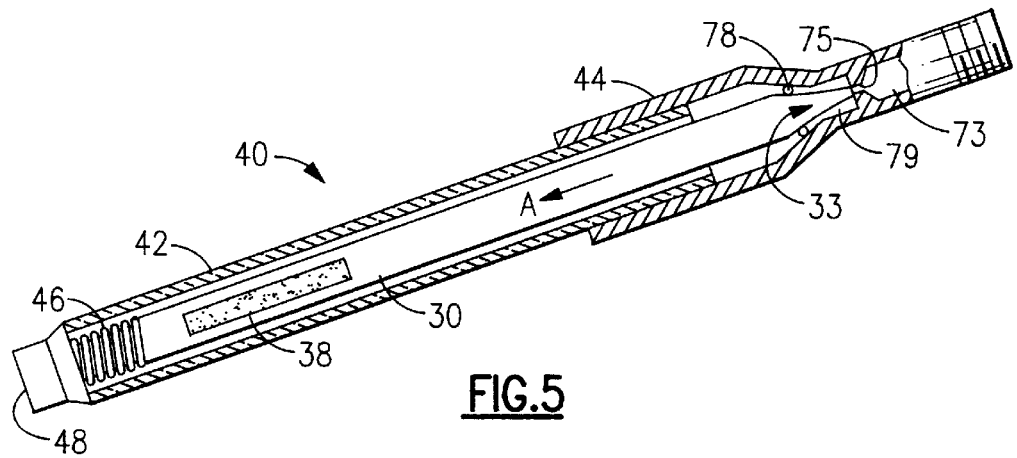
FIG. 5 is a partially cut away side elevation view of the contaminant testing tube holder apparatus depicted in FIG. 3.

The testing tube holder 40 comprises a tubular housing 42, an inlet fitting 44, and a bias device 46. The tubular housing 42, which is preferably made of a suitable transparent material, such as a polycarbonate or acrylic plastic, has an open outlet vent 48 at its distal end and an inside diameter sized to accept the testing tube 30 as best illustrated in FIGS. 3 through 5. The tubular housing 42 is removably mounted to the inlet fitting 44. Advantageously, bayonet connection means of a conventional type may be used for connecting the tubular housing 42 to the fitting 44 so that the tubular housing 42 may be easily and quickly removed from the fitting 44 for installation and removal of the testing tube 30. The bayonet groove of the bayonet connection means may be provided in the inside surface of the tubular housing 42 and the mating bayonet pin may be provided on the inside surface of the inlet fitting 44. It is to be understood that the groove-pin placement may be reserved, and also that a threaded connection or any other form of connection that permits ready connection and disconnection of the tubular housing 42 with the inlet fitting 44 may be used.

The inlet fitting 44 includes a flow restrictor means for controlling the amount of flow of refrigerant gas passed through the testing tube 30 during testing. The flow restrictor means may comprise, as depicted in FIG. 5, a small orifice 75 disposed at the downstream end of a converging passage 73 and opening into a substantially larger diameter flow passageway 79, the diameter of the flow passageway 79 preferably being substantially equal to the diameter of the flow passageway 35 of the testing tube 30. A sealing means, such as a resilient ring seal 78, is disposed within the inlet fitting 44 at the inlet end thereof downstream of the orifice 75. The bias device 46, which comprises an axially resilient member, advantageously a coil spring, disposed at the outlet end of the tubular housing, as best seen in FIG. 5, biases the test testing tube 30 towards the inlet end of the tubular housing 42 so as to seat and seal the testing tube 30 against the seal ring 78. In operation, the test sample flow of refrigerant from the compressor 10 passes through the hose 50 and the main flow passageway of the transitional tee 60 into the inlet fitting 44 and thence in a metered flow passes through the orifice 75 and thence, having traversed the orifice, passes through the testing tube 30 at a significantly reduced pressure much closer to atmospheric pressure than the compressor operating pressure. In a typical embodiment of the apparatus of the present invention, the diameter of the orifice 75 is sized to a refrigerant vapor flow of about 140 cc/min. to about 400 cc/min. through the testing tube 30 when the compressor refrigerant operating pressure is from about 70 psi to about 190 psi.

Figure 6:
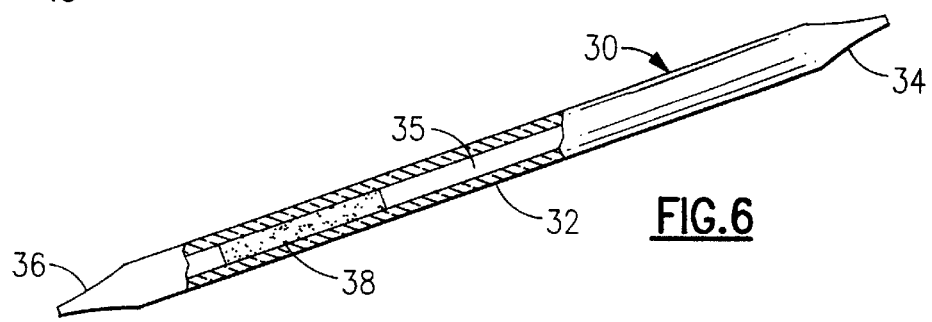
FIG. 6 is a partially cut away side elevation view of a contaminant testing tube.

Referring now to FIG. 6, the testing tube 30 for detecting the presence of hydrocarbon contaminants comprises a generally cylindrical tube 32 having two oppositely disposed tapered ends terminating, respectively, in a frangible inlet tip 34 and a frangible outlet tip 36. The tips 34 and 36 are intended to be broken off just prior to use thus forming an open flow inlet 33 and an open flow outlet at axially opposite ends of the flow passage 35 extending through the interior of the testing tube 30. Disposed within the testing tube 30 in the flow passage 35 is a chemical indicator medium 38 that contains a chemical which reacts with hydrocarbons so as to indicate the presence of hydrocarbon contaminants in a flow of non-hydrocarbon refrigerant vapor, for example, by changing color. A suitable chemical medium for use in indicating the presence of hydrocarbon compounds can be prepared from potassium dichromate, which has a yellow orange color, but reacts with hydrocarbons in the presence of sulfric acid to produce chromic sulfate which has a blackish green color. The chemical indicator medium 38 may, for example, comprise an open pore, flow pervious foam material impregnated with potassium dichromate. The mere presence of the hydrocarbon contaminant in the refrigerant vapor flow is revealed by the change in color per se, thus giving a qualitative indication that the CFC-12 or HFC-134a refrigerant is contaminated with a hydrocarbon. A testing tube containing an indicator medium impregnated with potassium dichromate for detecting the presence of hydrocarbon compounds is available from Sensidyne, Inc., of Clearwater, Fla. If a suitable indicating medium were available, a qualitative test could be made, for example, by matching the shade of the changed color of the indicating medium with the same shade of color on a precalibrated color coded card to give an approximate measurement of the level of hydrocarbon contaminant present in the refrigerant vapor sample flow. In a typical embodiment of the test apparatus of the present invention, the testing tube 30 is made of transparent glass and has an overall length of about 105 mm from tip to tip, a length of about 85 mm excluding the tapered end sections, an outside diameter about 6 mm, an inside diameter of about 4 mm, and an indicator medium extending for about 23 mm.

To perform a test for the presence of hydrocarbon compounds in a sample flow of nonhydrocarbon refrigerant, a testing tube 30 containing a chemical indicator medium 38 suitable for detecting the presence of hydrocarbons, is prepared for use by breaking off frangible tips 34 and 36 to produce open ends at the axially opposite open ends of the flow passage 35. The testing tube 30 is then placed into the inlet fitting 44 of the testing tube holder 40 such that the inlet end of the tube 30 rests against the seal ring 78. The tubular housing 42 is then slipped axially over the tube 30 and mounted to the inlet fitting 44, such as by means of a conventional bayonet. With the tubular housing 42 installed, the bias spring 46 exerts an axial bias force against the outlet end of the tube 30, thereby pushes the inlet end of the tube 30 to seat and seal against the seal ring 78.

With the hose 50 connected to the test apparatus 20, actual testing is commenced by connecting the connector 56 at the opposite end of the hose 50 to a service fitting on the compressor 10 of the system. Upon connection to the service fitting, a sample flow of refrigeration vapor begins to flow (in the direction of arrow A) from the closed system through the hose 50 and to the test apparatus. As the sample flow passes through the transitional tee fitting 60, the pressure is measured at a location upstream of the flow restrictor orifice 75 and indicated on the pressure gauge 70. A metered amount of refrigerant sample flow, typically for example about 150 cc/min., passes through the orifice 75 and thence passes through the flow passage 35 of the open ended testing tube 30 at a significantly reduced pressure much closer to atmospheric pressure. As the sample flow traverses the flow passage 35, the flow will traverse the chemical indicator medium 38 disposed within the testing tube 30. If the sample flow contains hydrocarbon compound contaminants, the presence of those contaminants will be indicated by a change in color of the chemical indicator medium 38. For example, when a hydrocarbon contaminant is present in a refrigerant vapor flow passing through the testing tube 30 and the chemical indicator medium 38 is impregnated with potassium dichromate, the color of the chemical indicator medium will change from its original burnt orange color to a shade of green. After traversing the testing tube 30, the sample refrigerant flow passes out of the open end 48 of the tubular holder 42 to vent to the atmosphere. The operator conducting the presence may detect the presence of ammonia in the refrigerant sample flow vented to the atmosphere by the characteristic pungent odor of ammonia.

The presence of undesirable HCFC-22 refrigerant, a hydrochlorofluorocarbon contaminant, in the non-hydrocarbon refrigerant, more specifically CFC-12 or HFC-134a refrigerant, is indicated by the pressure gauge 70. CFC-12 and HFC-134a refrigerants have a substantially lower saturation pressure at any given saturation temperature than the saturation pressure of HCFC-22 refrigerant at the same saturation temperature. For example, at a saturation temperature of 60° F., CFC-12 and HFC-134a each exhibit a saturation pressure of about 70 psia, while HCFC-22 has a saturation pressure of about 115 psia at a saturation temperature of 60° F.; and at a saturation temperature of 120° F., CFC-12 and HFC-134a exhibit saturation pressures of about 170 psia and 190 psia, respectively, while HCFC-22 has a saturation pressure of about 275 psia. Therefore, if the pressure indicated on the pressure gauge 70, is above that pressure that CFC-12 or HFC-134a would be expected to exhibit at the operating temperature, the presence of the higher saturation pressure hydrochlorofluorocarbon refrigerant HCFC-22 is indicated.

Although the method and apparatus of the present invention have been described with respect the particular embodiments illustrated, other embodiments may become apparent to one skilled in the art. For example, the present invention may be used not only for testing refrigeration, air conditioning and similar systems, but might also be adapted for testing other closed systems wherein hydrocarbon contaminants may be present. In addition, although the specification discloses a specific chemical for use in indicating the presence of hydrocarbon compounds, other suitable indicating media may be substituted for that disclosed. Further, although a specific embodiment of the testing tube holder is disclosed, other embodiments, including for example the testing tube holder disclosed in commonly assigned U.S. Pat. No. 5,174,964, may be used for supporting the testing tube during the course of a test procedure. Accordingly, it is intended that the present invention be limited only by the scope of the claims presented hereinafter.

What is claimed is:

1. A method for testing a non-hydrocarbon refrigerant in a closed system to detect the presence of hydrocarbons and the refrigerant HCFC-22 comprising the steps of:

withdrawing a sample of a non-hydrocarbon refrigerant from a closed system containing said non-hydrocarbon refrigerant;

measuring the pressure of said withdrawn sample to provide a first pressure measurement;

reducing the pressure of said withdrawn sample;

passing said reduced pressure sample through a testing tube;

providing in said testing tube a medium for indicating the presence of hydrocarbons in said sample passing through the testing tube and measuring the pressure of said sample after passing through the testing tube to provide a second pressure measurement, wherein the presence of the refrigerant HCFC-22 in the non-hydrocarbon refrigerant is indicated by a higher second pressure measurement in relation to the first pressure measurement.

2. A method as recited in claim 1 wherein said medium for indicating the presence of hydrocarbons comprises a chemical deposited on a surface disposed in the testing tube, said chemical having a characteristic of undergoing a change in color when contacted by a hydrocarbon.

3. A method as recited in claim 1 further comprising venting said sample of non-hydrocarbon refrigerant from the testing tube and detecting the presence of ammonia in said sample vented from the testing tube.

4. An apparatus for testing a non-hydrocarbon refrigerant in a closed system to detect contaminants comprising:

a testing tube having an axially enclosed body defining a passage therein and housing a medium for indicating the presence of hydrocarbon compounds, said tube body terminating at axially opposite closed tips, said closed tips being frangible to provide an open inlet and an open outlet to the passage;

a testing tube holder for supporting said testing tube during testing, said testing tube holder having an inlet section for receiving a flow of non-hydrocarbon refrigerant to be tested and directing a metered amount of said refrigerant flow through the testing tube passage, and an outlet end for venting said refrigerant flow from the testing tube passage in order to indicate the presence of ammonia in the non-hydrocarbon refrigerant; and a pressure gauge for indicating the pressure of said non-hydrocarbon refrigerant flow both before and after passing through said testing tube, wherein said pressure gauge serves to indicate the presence of HCFC-22 refrigerant in the non-hydrocarbon refrigerant when the pressure gauge indicates a higher pressure of said refrigerant flow after passing through said testing tube than before passing through said testing tube.

* * * * *